Figure 1:
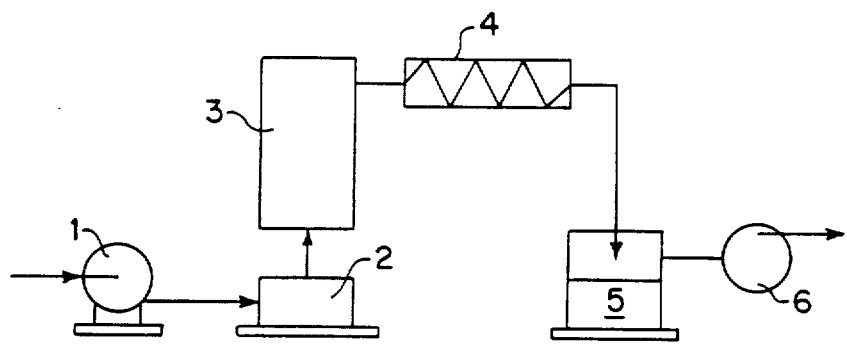

United States Patent [19]

Mahaim

[11] Patent Number: 4,967,033
[45] Date of Patent: Oct. 30, 1990

[54] PROCESS FOR THE PREPARATION OF POLYUNSATURATED CYCLIC COMPOUNDS

[75] Inventor: Cyril Mahaim, Echichens, Switzerland

[73] Assignee: Firmenich S.A., Geneva, Switzerland

[21] Appl. No.: 472,921

[22] Filed: Jan. 31, 1990

[30] Foreign Application Priority Data

Feb. 9, 1989 [CH] Switzerland ......................... 442/89-1

[51] Int. Cl.$^5$ ........................... C07C 1/32; C07C 2/76
[52] U.S. Cl. ..................................... 585/358; 585/360
[58] Field of Search ................................ 585/358, 360

[56] References Cited

U.S. PATENT DOCUMENTS 3,911,027 10/1975 Skoranetz ........................... 585/360
4,351,977 9/1982 Fehr ................................... 585/360

Primary Examiner—Helen M. S. Sneed
Assistant Examiner—J. Saba
Attorney, Agent, or Firm—Pennie & Edmonds

[57] ABSTRACT

The polyunsaturated compounds of formula

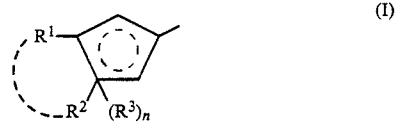

having two conjugated double bonds in the endo- and exo- positions of the pentagonal cycle indicated by the dotted lines, and wherein symbols $R^1$ and $R^2$, when taken separately, represent respectively a. a linear or brached $C_1$ to $C_4$ alkyl radical and b. an hydrogen atom or a methyl radical, or, when taken together with the carbon atoms to which they are bonded form a polymethylenic cycle such as indicated by the dotted line, containing from 5 to 12 carbon atoms, and symbol $R^3$ stands for an hydrogen atom or a methyl radical, n being an integer equal to 0 or 1, which are useful intermediate products for the preparation of odoriferous macrocyclic ketones, are prepared according to a process comprising a vapor phase cyclization of an enone of formula

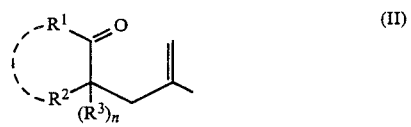

wherein the dotted line and the symbols n, $R^1$, $R^2$ and $R^3$ are defined as above, effected by means of a thermal treatment of said enone in the presence of a cyclization catalyst consisting of an aluminum, silicon, titanium or zirconium oxide.

5 Claims, No Drawings

PROCESS FOR THE PREPARATION OF POLYUNSATURATED CYCLIC COMPOUNDS

BRIEF SUMMARY OF THE INVENTION

The present invention relates to the field of organic synthesis. It concerns more particularly a process for the preparation of polyunsaturated cyclic compounds which are useful intermediate products in the synthesis of cyclic and macrocyclic odoriferous ketones, amongst which one can cite muscone.

According to the invention, a polyunsaturated cyclic compound of formula

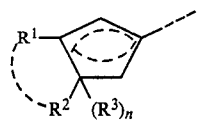

(I)

having two conjugated double bonds in the endo- and exo- positions of the pentagonal cycle indicated by the dotted lines, and wherein symbols $R^1$ and $R^2$, when taken separately, represent respectively a. a linear or branched $C_1$ to $C_4$ alkyl radical and b. an hydrogen atom or a methyl radical, or, when taken together with the carbon atoms to which they are bonded form a polymethylenic cycle such as indicated by the dotted line, containing from 5 to 12 carbon atoms, and symbol $R^3$ stands for an hydrogen atom or a methyl radical, n being an integer equal to 0 or 1, is prepared by a process comprising a vapor phase cyclization of an enone of formula

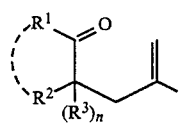

(II)

wherein the dotted line and the symbols n, $R^1$, $R^2$ and $R^3$ are defined as above, effected by means of a thermal treatment of said enone in the presence of a cyclization catalyst consisting of an aluminium, silicium, titanium or zirconium oxide.

BACKGROUND OF THE INVENTION

Muscone is a macrocyclic ketone well appreciated in the perfumery industry owing to its musky odor. A variety of processes for the preparation of muscone have been disclosed to this day. However, these prior art methods are not easily applied to large scale production, either because of their complexity, or owing to the low yields obtained in certain steps which are critical for the overall synthesis. One of the known processes makes use of the compounds of formula

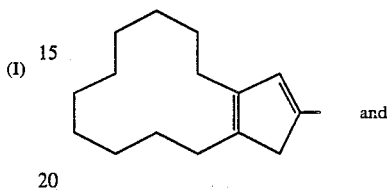

and

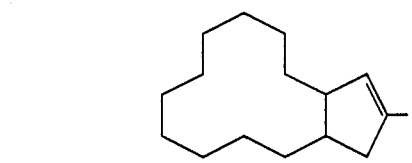

[see DE-OS 29 16 413, published on 6.11.1980], which compounds are subjected to hydrogenation, respectively acidic isomerisation, to give a compound of formula

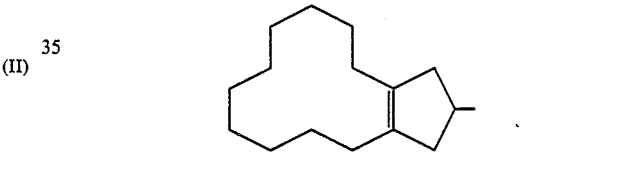

which, by ozonolysis followed by reduction, provides the desired muscone.

The starting products in the above-cited process were obtained by a multi-step synthesis illustrated in the following diagram:

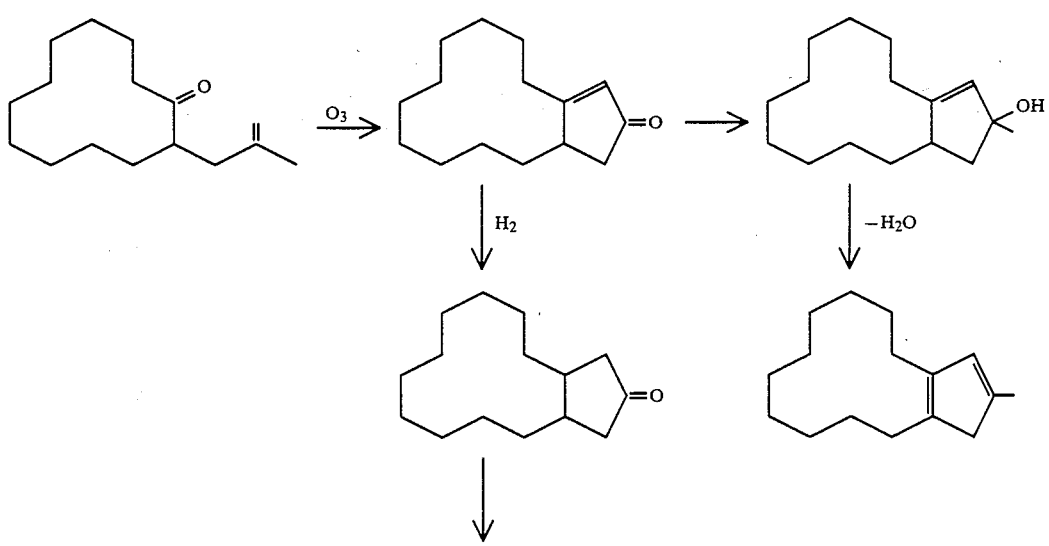

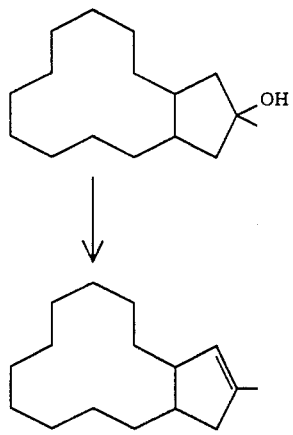

Another prior art process for the preparation of muscone resorts to the use of the compound of formula

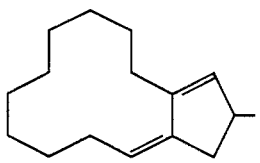

[see European patent No. 37116]. This compound was prepared by a process which comprises the addition of methallyl chloride to cyclododecanone, in alkaline medium, followed by the addition of thiophenol to the product thus obtained, oxidation by means of an organic peroxide and treatment of the resulting sulfone with a strong base.

The present invention provides a new process for the preparation of polyunsaturated cyclic compounds of formula

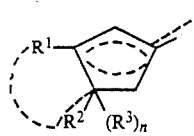  (I)

having two conjugated double bonds in the endo- and exo- positions of the pentagonal cycle indicated by the dotted lines, and wherein symbols $R^1$ and $R^2$, when taken separately, represent respectively a. a linear or branched $C_1$ to $C_4$ alkyl radical and b. an hydrogen atom or a methyl radical, or, when taken together with the carbon atoms to which they are bonded form a polymethylenic cycle such as indicated by the dotted line, containing from 5 to 12 carbon atoms, and symbol $R^3$ stands for an hydrogen atom or a methyl radical, n being an integer equal to 0 or 1.

THE INVENTION

According to the process of the invention, an enone of formula

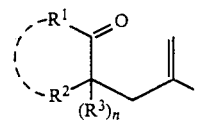  (II)

wherein the dotted line and the symbols n, $R^1$, $R^2$ and $R^3$ are defined as above, is subjected to a vapor phase cyclization, by means of a thermal treatment of said enone in the presence of a cyclization catalyst consisting of a aluminum, silicium, titanium or zirconium oxide.

Without precluding the correctness of the mechanistic interpretation of the process, we presume that the reaction proceeds according to an intramolecular "ene" reaction scheme as shown below:

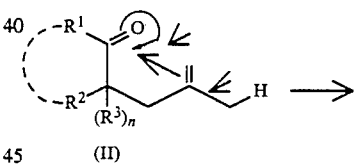

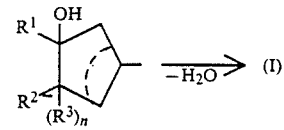

The process of the invention is carried out, preferably, at a temperature having a value between 200° and 400° C., although the best yields in the desired products were obtained with temperatures ranging from around 280° to 320° C. At lower temperatures we observed an increasing yield in side products in the form of cyclic ethers represented by the formula

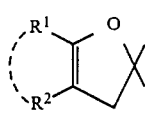

while temperatures above the cited upper limit showed decreasing yields in the desired products, presumably as a result of cracking reactions.

Preferably, the cyclization reaction is carried out at reduced pressure. The pressure value used is chosen so as to allow a compromise between the fact that an adequate and constant flow of the vapors from the starting enone is necessary and that the vapors formed should be in contact with the catalyst for a sufficient amount of time to provide a satisfactory conversion.

We have been able to determine that pressures comprised between $1 \times 10^3$ and $13 \times 10^3$ Pa are perfectly adequate for this purpose. However, the reaction can take place at pressures above the cited limits and, namely, at atmospheric pressure.

A particular embodiment of the apparatus adapted to carry out the process of the invention is represented, by way of example, in the attached drawing.

The figure represents a diagram of said apparatus. The starting enone is inserted in a pre-heating oven 2 by means of a dosing pump 1 and the vapors thus formed are forced to pass through the catalyst contained in a heated column 3. The vapors from the resulting product are then condensed by means of a cooling and trapping system 4 and collected in a container 5. The desired pressure level is achieved with a suction pump 6.

As it is indicated above, the vapors from the starting enone get into contact with the cyclization catalyst contained in a column pre-heated to the chosen reaction temperature. The flow of said enone vapors in the catalyst column is kept at a constant value, on the one hand by means of the suction applied to the column and, on the other hand, by means of a regular input of liquid enone achieved with a dosing pump.

The desired product, in admixture with unreacted starting enone, is then collected by condensation of the vapors coming out of the column.

Amongst the catalysts capable of promoting the cyclization of the starting product, one can cite alunina, silica, $ZrO_2$, ZnO and $TiO_2$. Without exception, these are commercially available products. Alumina is the preferred catalyst.

The ratio between the amount of catalyst and that of starting product is not critical and it can vary in a wide range of values. Ratios of the order of 1:52 (alumina:enone) have been used without any noticeable reduction in yield. In the same way, the flow value of the enone vapors circulating through the column can vary without substantially affecting the cyclization yields. A flow of 0.2–1 ml of enone per ml of useful volume and per hour, and preferably 0.4 to 0.6, is perfectly adequate under the circumstances. The useful volume is defined as the volume occupied by the catalyst in the column which contains it.

The invention is illustrated in greater detail by way of the following non-restrictive examples (temperatures are indicated in degrees centigrade and the abbreviations have the usual meaning in the art).

The apparatus used in the process of the invention is schematically represented in the attached drawing.

EXAMPLE 1

Preparation of 14-methyl-bicyclo[10.3.0]pentadeca-1(12),13-diene

The catalyst column had a useful volume of 50 ml and was charged with 22.5 g of alumina ($Al_2O_3$, Harshaw Al 3996 R). 1300 g of 2-(2-methyl-2-propenyl)-cyclododecanone or methallylcyclododecanone were introduced into an evaporator by means of a dosing pump adjusted so as to provide a flow of 10 ml/h. The evaporator was maintained at a temperature of 260° and the pressure applied was $1.1 \times 10^4$ Pa. The column charged with alumina was kept at a constant temperature of about 260°. The resulting vapors were then condensed by means of a refrigerant and the desired product was separated by decantation (yield: 94%).

The same procedure was followed using as a catalyst one of the following metal oxides:

gamma-$Al_2O_3$ Akzo 001-3 P
gamma-$Al_2O_3$ Akzo 001-1.5 E
gamma-$Al_2O_3$ BASF D10-10
gamma-$Al_2O_3$ BASF D10-20
gamma-$Al_2O_3$ Rhône-Poulenc SAS 350
$SiO_2$ BASF D11-10
gamma-$Al_2O_3$/$H_3PO_4$ Harshaw
$ZrO_2$ Harshaw
ZnO BASF
$TiO_2$ Harshaw The reaction was also carried out at 250° and 300°. The experiments showed that the cyclization of methallylcyclododecanone proceeded in much the same way, without noticeable variations, within the limits of the chosen conditions.

NMR($^1$H, 360 MHz, $CDCl_3$): 1.00–1.80(m, 16H); 2.00(b.s, 3H); 2.26(t, J=6 Hz, 2H); 2.34(t, J=6 Hz, 2H); 2.79(b.s, 2H); 5.96(b.s, 1H) δ ppm.

MS: 218(6, M+), 203(1), 189(0), 175(1), 161(4), 147(0), 133(11), 119(24), 107(39), 94(100), 91(40), 79(19), 67(6), 55(8), 41(7).

EXAMPLE 2

Preparation of 4,5,6,7-tetrahydro-2-methyl-1H-indene

The catalyst column had a useful volume of 20 ml and was charged with 9.0 g of alumina ($Al_2O_3$, Harshaw Al 3996 R). 100 g of 2-(2-methyl-2-propenyl)-cyclohexanone or methallylcyclohexanone were introduced into an evaporator by means of a dosing pump adjusted so as to provide a flow of 8.5 ml/h. The evaporator was maintained at a temperature of 270° to 290° and the pressure applied was $1.1 \times 10^4$ Pa. A flow of water of 3 ml/h was simultaneously fed to preserve the catalyst's life.

The resulting vapors were then condensed by means of a refrigerant and a mixture of the desired product with other isomers thereof was obtained (yield: 72%). The desired compound, representing about 40% by weight of the said mixture, was separated by distillation of a Fischer column.

B. p. 65°/$1.5 \times 10^3$ Pa.

NMR($^1$H, 360 MHz, $CDCl_3$): 1.60–1.80(b.s., 4H); 2.05(b.s, 3H); 2.10–2.35(m, 4H); 2.75(b.s, 2H); 5.90(b.s, 1H) δ ppm.

MS: 134(28, M+), 119(33), 106(38), 105(43), 91(100).

EXAMPLE 3

Preparation of 4,5,6,7-tetrahydro-2,3a,7,7-tetramethyl-3aH-indene

The catalyst column had a useful volume of 20 ml and was charged with 9.6 g of alumina ($Al_2O_3$, Harshaw Al 3996 R). 38.5 g of 2,2,6-trimethyl-6-(2-methyl-2-propenyl)-cyclohexanone were introduced into an evaporator by means of a dosing pump adjusted so as to provide a flow of 8.3 ml/h. The evaporator was maintained at a temperature of 270° and the pressure applied was $1.6 \times 10^3$ Pa.

The resulting vapors were then condensed by means of a refrigerant and 20.8 g of a mixture containing about 60% by weight of the desired product, 20% by weight of unreacted starting enone and 12% of an unidentified isomer of the desired product were obtained.

The desired compound was separated from the mixture by distillation on a Fischer column.

B. p. 88°–89°/1.6×10³ Pa.

NMR($^1$H, 360 MHz, CDCl$_3$): 0.85–1.23(m, 2H); 1.13(s, 3H); 1.14(s, 3H); 1.45–1.95(m, 4H); 1.85(b.s, 3H); 5.74(b.s, 1H); 5.76(b.s, 1H) δ ppm.

MS: 176(5, M$^+$), 161(100), 147(2), 133(11), 119(20), 105(13), 91(14), 77(5).

EXAMPLE 4

Preparation of 1,3-dimethyl-1,3-cyclopentadiene

The catalyst column had a useful volume of 30 ml and was charged with 16.1 g of alumina (Al$_2$O$_3$, Harshaw Al 3996 R). 354 g of 5-methyl-5-hexen-2-one were introduced into an evaporator at atmospheric pressure and at a temperature kept at 260° to 280°. The temperature was increased during the reaction in order to maintain the conversion. Water was simultaneously fed at a flow of 3 ml/h, the flow in starting enone being 15 ml/h.

The resulting vapors were then condensated by means of a refrigerant and 271 g of a mixture containing about 80% by weight of the desired compound and small quantities of other isomers, as well as of starting ketone, were obtained.

The desired product was separated by distillation at atmospheric pressure.

B. p. 62°/1×10⁵ Pa.

NMR($^1$H, 360 MHz, CDCl$_3$): 1.95(b.s, 3H); 2.05(b.s, 2H); 2.85(m, 2H); 5.70(b.s, 1H); 5.00(b.s, 1H) δ ppm.

MS: 94(46, M$^+$), 93(77), 91(29), 77(56).

EXAMPLE 5

Preparation of 1,3,5,5-tetramethyl-1,3-cyclopentadiene (a) 3,3-dimethyl-5-methyl-5-hexen-2-one 93 g of NaOH, 12 g of NaI and 6.8 g of Emkapol 400 (polyethyleneglycol) were charged into a 1 l three-neck flask. 100 g of methylisopropyl ketone were added and, at 50°, 290 g of methallyl chloride. The mixture was heated to reflux for 4 h and then hydrolysed with 200 ml of water. The reaction product was washed to neutrality and distilled to provide 69.6 g of raw product (B. p. 56°–65°/5.0×10³ Pa). Distillation of this raw product on a Widmer column gave 44.5 g of the desired ketone.

B. p. 57°–60°/3×10³ Pa.

NMR($^1$H, 360 MHz, CDCl$_3$): 1.15(s, 6H); 1.65(s, 3H); 2.15(s, 3H); 2.30(s, 2H); 4.65(s, 1H); 4.80(s, 1H) δ ppm.

MS: 160(20, M$^+$), 125(8), 197(11), 97(64), 83(8), 69(33), 55(100), 43(44).

(b) The catalyst column had a useful volume of 20 ml and was charged with 10.8 g of alumina (Al$_2$O$_3$, Harshaw Al 3996 R). 48.2 g of 3,3-dimethyl-5-methyl-5-hexen-2-one prepared according to a) were introduced into an evaporator by means of a dosing pump adjusted so as to provide a flow of 10 ml/h, with water being fed simultaneously at a flow of 7 ml/h. After condensing the resulting vapors, a mixture was obtained, containing 80% by weight of the desired cyclopentadiene and some minor products. Purification of this mixture on a Fischer column provided the desired pure cyclopentadiene.

B. p. 37°/5.0×10⁴ Pa.

NMR($^1$H, 360 MHz, CDCl$_3$): 1.02(s, 6H); 1.78(d, J=2 Hz, 2H); 1.86(d, J=2 Hz, 2H); 5.71(b.s, 1H); 5.75(b.s, 1H) δ ppm.

MS: 122(35, M$^+$), 107(160), 91(56), 79(39), 77(14), 65(10).

What we claim is:

1. A process for the preparation of a polyunsaturated cyclic compound of formula

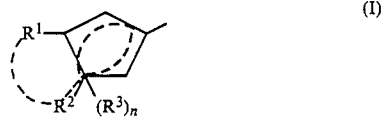

(I)

having two conjugated double bonds in the endo- and exo- positions of the pentagonal cycle indicated by the dotted lines, and wherein symbols R$^1$ and R$^2$, when taken separately, represent respectively a. a linear or branched C$_1$ to C$_4$ alkyl radical and b. an hydrogen atom or a methyl radical, or, when taken together with the carbon atoms to which they are bonded form a polymethylenic cycle such as indicated by the dotted line, containing from 5 to 12 carbon atoms, and symbol R$^3$ stands for an hydrogen atom or a methyl radical said process comprising a vapor phase cyclization of an enone of formula

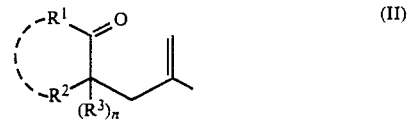

(II)

wherein the dotted line and the symbols n, R$^1$, R$^2$ and R$^3$ are defined as above, effected by means of a thermal treatment of said enone in the presence of a cyclization catalyst consisting of an aluminum, silicium, titanium or zirconium oxide.

2. A process according to claim 1, wherein said cyclization catalyst is alumina.

3. A process according to claim 1, wherein said cyclization is carried out at a temperature between 200° and 400° C.

4. A process according to claim 3, wherein said cyclization is carried out at a temperature between 280° and 320° C.

5. A process according to claim 1, wherein the cyclization is carried out at a reduced pressure between 1×10³ Pa and 13×10³ Pa.

* * * * *

UNITED STATES PATENT AND TRADEMARK OFFICE
CERTIFICATE OF CORRECTION

PATENT NO. : 4,967,033

DATED : October 30, 1990

INVENTOR(S) : Cyril Mahaim

It is certified that error appears in the above-identified patent and that said Letters Patent is hereby corrected as shown below:

Formula (I) in the Abstract, and at column 1, lines 15-20; column 3, line 50 and column 8, lines 15-20 should be corrected to:

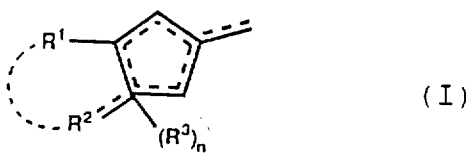

In the abstract, on line 7, change "brached" to --branched--

In column 4, the reaction scheme between lines 40 and 50 should appear as follows:

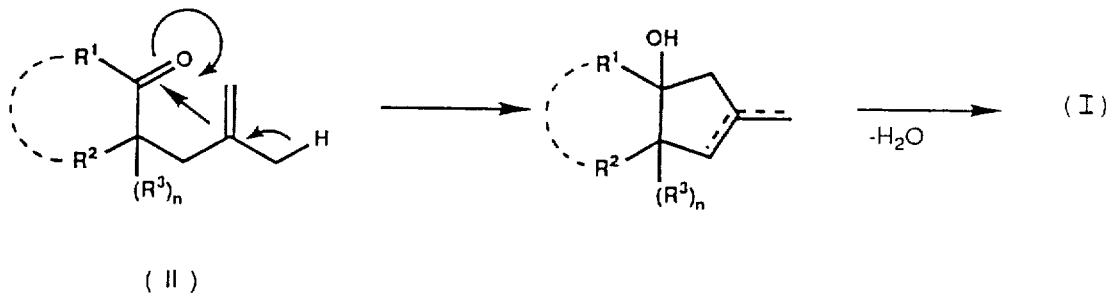

UNITED STATES PATENT AND TRADEMARK OFFICE
CERTIFICATE OF CORRECTION

PATENT NO. : 4,967,033

DATED : October 30, 1990

INVENTOR(S) : Cyril Mahaim

It is certified that error appears in the above-identified patent and that said Letters Patent is hereby corrected as shown below:

In column 5, line 36, change "alunina" to --alumina--.

Add the attached drawing figure, which is described at column 5, lines 13-23.

Signed and Sealed this

Twenty-third Day of June, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,967,033

DATED : October 30, 1990

INVENTOR(S) : Cyril Mahaim

It is certified that error appears in the above-identified patent and that said Letters Patent is hereby corrected as shown below:

At Column 5, line 15: insert -- BRIEF DESCRIPTION OF THE DRAWING --

At Column 5, between lines 16 and 17; insert -- DETAILED DESCRIPTION OF THE INVENTION --

Signed and Sealed this

Twenty-second Day of June, 1993

Attest:

MICHAEL K. KIRK

Attesting Officer

Acting Commissioner of Patents and Trademarks